United States Patent [19]
Rise et al.

[11] Patent Number: 5,833,709
[45] Date of Patent: Nov. 10, 1998

[54] METHOD OF TREATING MOVEMENT DISORDERS BY BRAIN STIMULATION

[75] Inventors: Mark T. Rise, Monticello; Gary W. King, Fridley, both of Minn.

[73] Assignee: Medtronic, Inc., Minneapolis, Minn.

[21] Appl. No.: 848,319

[22] Filed: Apr. 30, 1997

Related U.S. Application Data

[62] Division of Ser. No. 637,366, Apr. 25, 1996, Pat. No. 5,716,377.

[51] Int. Cl.$^6$ ..................................................... A61N 1/00
[52] U.S. Cl. ................................................................. 607/2
[58] Field of Search ................................... 607/2, 45, 48; 600/378

[56] References Cited

U.S. PATENT DOCUMENTS

| | | |
|---|---|---|
| 3,850,161 | 11/1974 | Liss ............................................ 607/45 |
| 3,918,461 | 11/1975 | Cooper . |
| 3,920,024 | 11/1975 | Bowers . |
| 3,957,036 | 5/1976 | Normann . |
| 4,524,774 | 6/1985 | Hildebrandt . |
| 4,570,640 | 2/1986 | Barsa . |
| 4,580,569 | 4/1986 | Petrofsky . |
| 4,690,145 | 9/1987 | King-Smith . |
| 4,702,254 | 10/1987 | Zabara ...................................... 607/45 |
| 4,750,499 | 6/1988 | Hoffer . |
| 4,838,272 | 6/1989 | Liebar . |
| 4,867,164 | 9/1989 | Zabara . |
| 4,909,255 | 3/1990 | Farin . |
| 5,002,053 | 3/1991 | Garcia-Rill et al. . |
| 5,025,807 | 6/1991 | Zabara . |
| 5,058,584 | 10/1991 | Bourgeois . |
| 5,154,172 | 10/1992 | Terry, Jr. et al. ........................ 607/45 |
| 5,167,229 | 12/1992 | Peckham . |
| 5,293,879 | 3/1994 | Vonk et al. . |
| 5,304,206 | 4/1994 | Baker, Jr. et al. ......................... 607/2 |
| 5,314,458 | 5/1994 | Najafi . |
| 5,330,505 | 7/1994 | Cohen . |
| 5,370,672 | 12/1994 | Fowler et al. . |
| 5,540,734 | 7/1996 | Zabara ...................................... 607/45 |
| 5,683,422 | 11/1997 | Rise ............................................ 607/2 |

FOREIGN PATENT DOCUMENTS

| | | |
|---|---|---|
| 0236513 | 9/1987 | European Pat. Off. . |
| WO 95/19804 | 7/1995 | WIPO . |

OTHER PUBLICATIONS van Horne et al., "Mulichannel Semiconductor–Based Electrodes for In Vivo Electrochemical and Electrophysiological Studies in Rat CNS". *Neuroscience Letters*. 120. pp. 249–252 (1990).

Alexander et al., "Basal Ganglia–Thalamocortical Circuits: Parallel Substrates for Motor. Oculomotor, 'Prefrontal' and 'Limbic' Functions". *Progress in Brain Research*, vol. 85: 119–146.

Bergman et al., "Reversal of Experimental Parkinsonism by Lesions of the Subthalamic Nucleus" *Science*, vol. 249: 1436–1438 (Sep. 21, 1990).

Benabid et al., "Long term Suppression of Tremor by Chronic Stimulation of the Ventral Intermediate Thalamic Nucleus", *The Lancet*, vol. 337: 403–406 (Feb. 16, 1991).

Limousin et al., "Effect on Parkinsonian Signs and Symptoms of Bilateral Subthalamic Nucleus Stimulation", *The Lancet*, vol. 345: 91–95 (Jan. 14, 1995).

Benabid et al., "Chronic Electrical Stimulation of the Ventralis Intermedius Nucleus of the Thalamus as a Treatment of Movement Disorders", *J. Neurosurg.*, vol. 84: pp. 203–214 (Feb. 1996).

*Primary Examiner*—William E. Kamm
*Assistant Examiner*—George R. Evansko
*Attorney, Agent, or Firm*—Banner & Witcoff Ltd.

[57] ABSTRACT

Techniques for stimulating the brain to treat movement disorders resulting in abnormal motor behavior by means of an implantable signal generator and electrode. A sensor is used to detect the symptoms resulting from the motion disorder. A microprocessor algorithm analyzes the output from the sensor in order to regulate the stimulation delivered to the brain.

19 Claims, 8 Drawing Sheets

METHOD OF TREATING MOVEMENT DISORDERS BY BRAIN STIMULATION

This is a divisional of application Ser. No. 08/637,366, filed Apr. 25, 1996, now U.S. Pat. No. 5,716,377 for which priority is claimed.

BACKGROUND OF THE INVENTION

1. Field of the Invention

This invention relates to brain stimulation techniques, and more particularly relates to such techniques for treating movement disorders.

2. Description of Related Art

Patients with neurodegenerative diseases or trauma like cerebral infarct or spinal cord injury can have a variety of movement and muscle control problems, like resting, postural, intention or action tremor, dystonia (improper muscle tone, myoclonus); spasticity (undesirable movements, or muscle co-contraction), dyskinesia (poorly executed movements) or involuntary movements like ballismus, choreiform movements and torticollis (inappropriate movements or limb control). Many of these problems can be called hyperkinesia. Although they can be chronic, or worse, progressive, they also may have times of relative remission. Such problems are found, at certain stages, for patients with Parkinson's disease, multiple sclerosis, cerebral palsy, secondary to deafferentation pain, post stroke, post apoplexy or anoxia, post head or spinal trauma, post poisoning, cerebellar disease, etc. Dyskinesia also may result from long term usage of L-dopa, or Levodopa, for Parkinson's patients, or other drugs.

Spasticity is defined as a state of excessive muscular tonus (hypertonus) and increased spinal reflexes. This condition exists when the corticospinal pathways have been disrupted. Disruption can occur as a result of stroke causing injury to the fibers as they pass through the internal capsule, a degenerative disorder or physical trauma to the cortex or spinal cord. Loss of this pathway leads to a lack of inhibition of the lower motorneurons which then are more active and responsive to reflexes In some cases injury to the premotor cortex disrupts the output of the primary motor cortex leading to the similar phenomena.

One form of the Dyskinesia is known as Ballism which typically results in violent flinging movements of the limbs. The movements often affect only one side of the body, in which case the disorder is known as Hemiballism.

In patients suffering from essential tremor or tremor due to Parkinson's Disease, the predominant symptom of the disordered movement is tremor. Tremor is often subdivided on the basis of whether the trembling of the limb occurs when the limb is at rest or when muscular contraction is occurring.

Besides being caused by degenerative illness or head injury, tremor can be of unknown origin. One syndrome of idopathic tremor is referred to as essential tremor.

Patients with neurodegenerative diseases or trauma to the basal ganglia like cerebral infarct can have a variety of movement and muscle control problems, like akinesia, rigidity or bradykinesia. These motor disorders may be called hypokinetic problems, the inability to move. These problems can be chronic, or worse, progressive, but they also may have times of relative remission, especially when drugs are effective. Such problems are common, at certain stages, for patients with Parkinson's disease, multiple sclerosis, cerebral palsy, secondary to deafferentation pain, post stroke, post apoplexy or anoxia, post head or spinal trauma, post poisoning, cerebellar disease, etc. Dyskinesia is often a side-effect from medications used for certain symptoms (like tremor, akinesia, rigidity), especially L-dopa or Levodopa.

Neurosurgeons have been able to diminish the symptoms of the foregoing movement disorders by lessening certain brain areas. In addition, it has been demonstrated that Deep Brain Stimulation (DBS) at high frequencies (100 Hz or higher) of certain brain structures can alleviate, diminish, or completely stop symptoms of tremor, rigidity, akinesia or hemiballism. Published targets of stimulation include the VIM (ventral intermediate thalamus), subthalamic nucleus and internal globus pallidus.

It is believed that many symptoms of the foregoing motion disorders are due to dysfunction of the basal ganglia or thalamus. The dysfunction can result in overactivity of the output neurons of the ganglia creating excessive inhibition of the thalamus or underactivity of the ganglia resulting in too little inhibition of the thalamus. If there is too little output activity from the basal ganglia or too little inhibition of the thalamus, a condition such as Ballism or Dystonia will result. If there is too much output activity from the basal ganglia (too much inhibition), a condition such as Hypokinesia will result.

SUMMARY OF THE INVENTION

A preferred form of the invention can treat a movement disorder resulting in abnormal motor response by means of an implantable signal generator and an implantable electrode having a proximal end coupled to the signal generator and having a stimulation portion for therapeutically stimulating the brain. The electrode is implanted in the brain so that the stimulation portion lies adjacent to a predetermined site in the basal ganglia or thalamus of the brain. The signal generator is operated to pulse the electrode at a predetermined rate and amplitude. By using the foregoing method, the symptoms of hypokinetic disorders, such as Akinesia, Bradykinesia or Rigidity, and hyperkinetic disorders, such as Ballism, Hemiballism, Choreiform, Torticollis, Spasticity or Dystonia can be alleviated. According to one embodiment of the invention, the stimulation can decrease excitement of the thalamus or increase inhibition of the thalamus. According to another embodiment of the invention, the stimulation can increase excitement of the thalamus or decrease inhibition of the thalamus.

Another form of the invention uses a sensor in combination with a signal generator and a stimulating electrode to treat a movement disorder resulting in abnormal motor behavior. In this form of the invention, the sensor generates a sensor signal relating to the extent of the abnormal motor behavior. Control means responsive to the sensor signal regulate the signal generator so that the stimulation is increased in response to an increase in the abnormal motor behavior and is decreased in response to a decrease in the abnormal motor behavior.

By using the foregoing techniques, the symptoms of hypokinetic disorders, such as akinesia, bradykinesia or rigidity, and hyperkinetic disorders, such as ballism or hemiballism, chorea, athetosis, spasticity, or dystonia can be alleviated.

BRIEF DESCRIPTION OF THE DRAWINGS

These and other advantages and features of the invention will become apparent upon reading the following detailed description and referring to the accompanying drawings in which like numbers refer to like parts throughout and in which.

DESCRIPTION OF THE PREFERRED EMBODIMENTS

Figure 1:
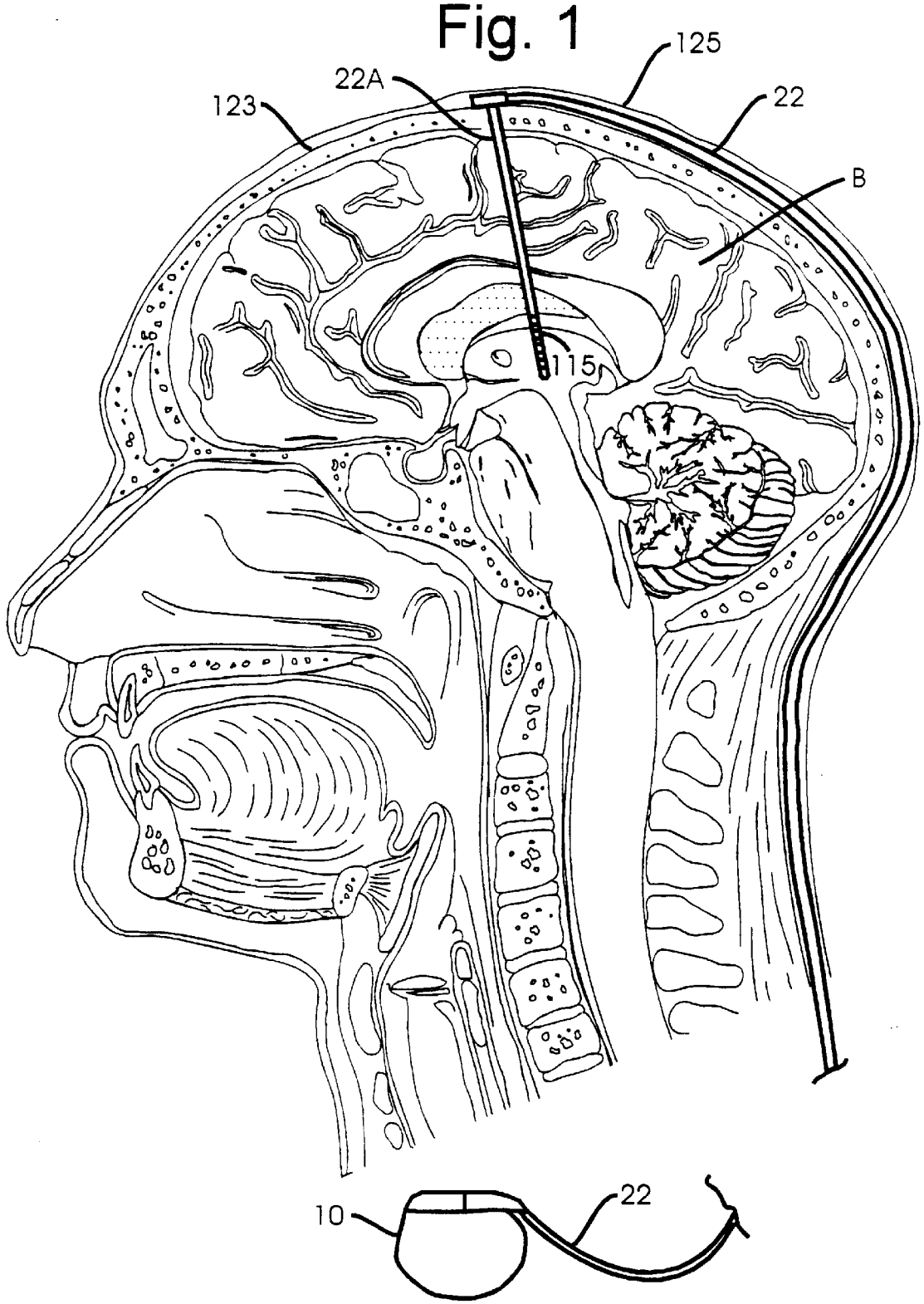
FIG. 1 is a diagrammatic illustration of an electrode implanted ;n a brain according to a preferred embodiment of the present invention and a signal generator coupled to the electrode.

Referring to FIG. 1, a system or device 10 made in accordance with the preferred embodiment may be implanted below the skin of a patient. A lead 22A is positioned to stimulate a specific site in a brain (B). Device 10 may take the form of a modified signal generator Model 7424 manufactured by Medtronic, Inc. under the trademark Itrel II which is incorporated by reference. Lead 22A may take the form of any of the leads sold with the Model 7424, for stimulating the brain, and is coupled to device 10 by a conventional conductor 22.

Figure 2:
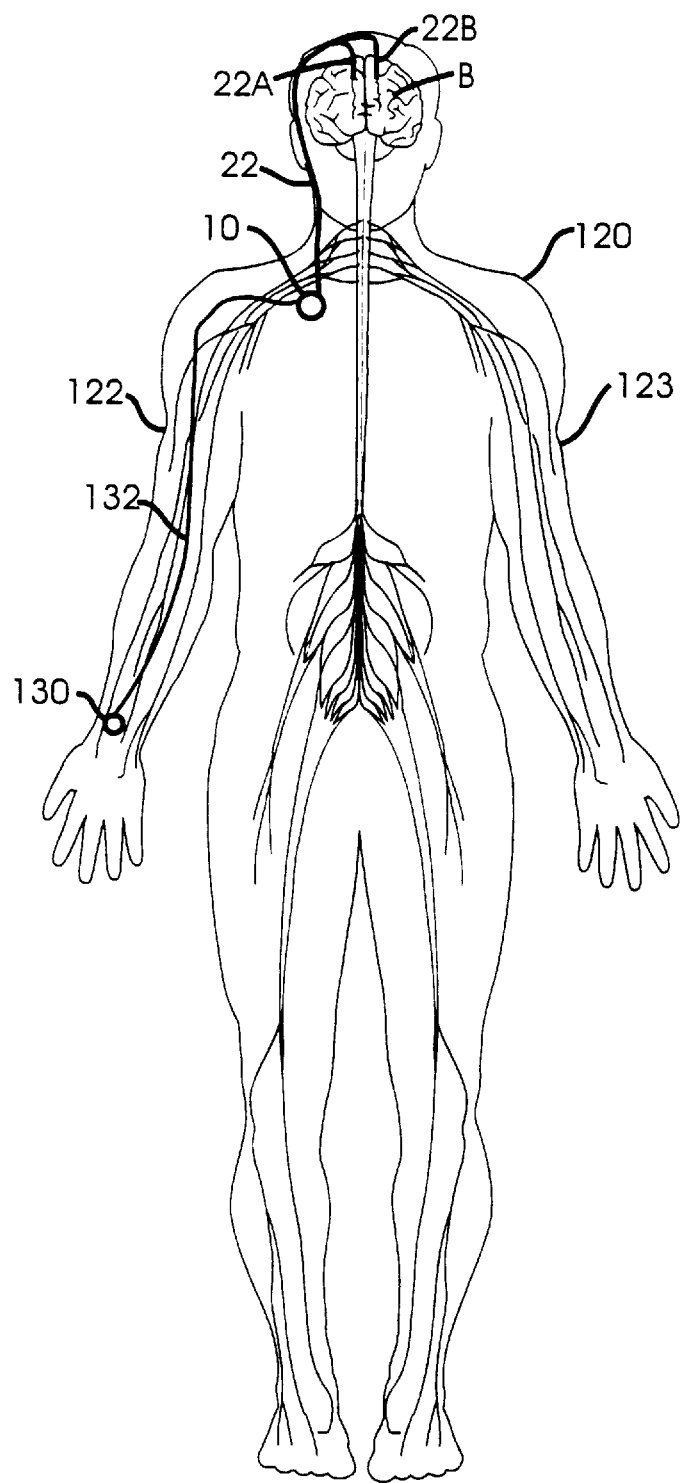
FIG. 2 is a diagrammatic illustration of a portion of the nervous system of the human body in which a preferred form of motion sensor, signal generator and electrode have been implanted.

The distal end of lead 22A terminates in four stimulation electrodes generally designated I1 5 implanted into a portion of the basal ganglia of the brain by conventional stereotactic surgical techniques. However, other numbers of electrodes, such as two or six, may be used for various applications. Each of the four electrodes is individually connected to device 10 through lead 22A and conductor 22. Lead 22A is surgically implanted through a hole in the skull 123 and conductor 22 is implanted between the skull and the scalp 125 as shown in FIG. 1. Conductor 22 is joined to implanted device 10 in the manner shown. Referring to FIG. 2, device 10 is implanted in a human body 120 in the location shown. Body 120 includes arms 122 and 123. Alternatively, device 10 may be implanted in the abdomen.

Conductor 22 may be divided into twin leads 22A and 22B that are implanted into the brain bilaterally as shown. Alternatively, lead 22B may be supplied with stimulating pulses from a separate conductor and signal generator. Leads 22A and 22B could be 1) two electrodes in two separate nuclei that potentiate each others effects or 2) nuclei with opposite effects with the stimulation being used to fine tune the response through opposing forces.

A sensor 130 is attached to or implanted into a portion of a patient's body suitable for detecting symptoms of the motion disorder being treated, such as a motor response or motor behavior. In this specification and claims, motor behavior includes motor response. Sensor 130 is adapted to sense an attribute of the symptom to be controlled or an important related symptom. For motion disorders that result in abnormal movement of an arm, such as arm 122, sensor 130 may be a motion detector implanted in arm 122 as shown. For example, sensor 130 may sense three-dimensional or two-dimensional motion (linear rotational or joint motion), such as by an accelerometer. One such sensor suitable for use with the present invention is described in U.S. Pat. No. 5,293,879 (Vonk). Another suitable accelerometer is found in pacemakers manufactured by Medtronic, Inc. and described in patent application Ser. No. 08/399072 filed Mar. 8, 1995, now U.S. Pat. No. 5,674,258 in the names of James Sikorski and Larry R. Larson and entitled "Package Integrated Accelerometer" Sensor 130 also may be placed in device 10 in order to detect abnormal movement resulting from the motion disorder being treated.

Sensor 130 also may be capable of detecting gravity direction or motion relative to some object (e.g., a magnet) either implanted or fixed nearby. Sensor 130 also may take the form of a device capable of detecting force in muscles or at joints, or pressure.

Sensor 130 may detect muscle EMG in one, two or more muscles, or in reciprocal muscles at one joint. For such detection, sensor 130 may take the form of a recording electrode inserted into the muscle of interest.

Brain EEG (e.g., motor cortex potentials recorded above the motor neurons controlling specific muscle groups) also may be detected by sensor 130.

Yet another form of sensor 130 would include a device capable of detecting nerve compound action potentials (e.g., either sensory afferent information from muscle or skin receptors or efferent motor potentials controlling a muscle of interest).

For certain types of patients, sensor 130 may take the form of device detecting the posture of the patient.

Sensor 130 also may take the form of a device capable of detecting nerve cell or axon activity that is related to the pathways at the cause of the symptom, or that reflects sensations which are elicited by the symptom. Such a sensor may be located deep in the brain. For such detecting, sensor 130 may take the form of an electrode inserted into the internal capsule of the brain, or other locations that are part of the basal ganglia. Signals that are received by the sensor may by amplified before transmission to circuitry contained within device 10.

Sensor 130 may take the form of a transducer consisting of an electrode with an ion selective coating applied which is capable of directly transducing the amount of a particular transmitter substance or its breakdown by-products found in the interstitial space of a region of the brain such as the ventral lateral thalamus. The level of the interstitial transmitter substance is an indicator of the relative activity of the brain region. An example of this type of transducer is described in the paper "Multichannel semiconductor-based electrodes for in vivo electrochemical and electrophysiological studies in rat CNS" by Craig G. van Home, Spencer Bement, Barry J. Hoffer, and Greg A. Gerhardt, published in *Neuroscience Letters*, 120 (1990) 249–252.

For tremor, the relative motion of a joint or limb or muscle EMG may be productively sensed Sensing electrical activity of neurons in various locations of the motor circuitry also is helpful Recording the electrical activity in the thalamus or cerebellum will reveal a characteristic oscillating electrical activity when tremor is present.

For Ballism, Hemiballism or tremor, sensor 130 may take the form of an accelerometer detecting relative motion of a joint and limb or muscle EMG.

Figure 3:
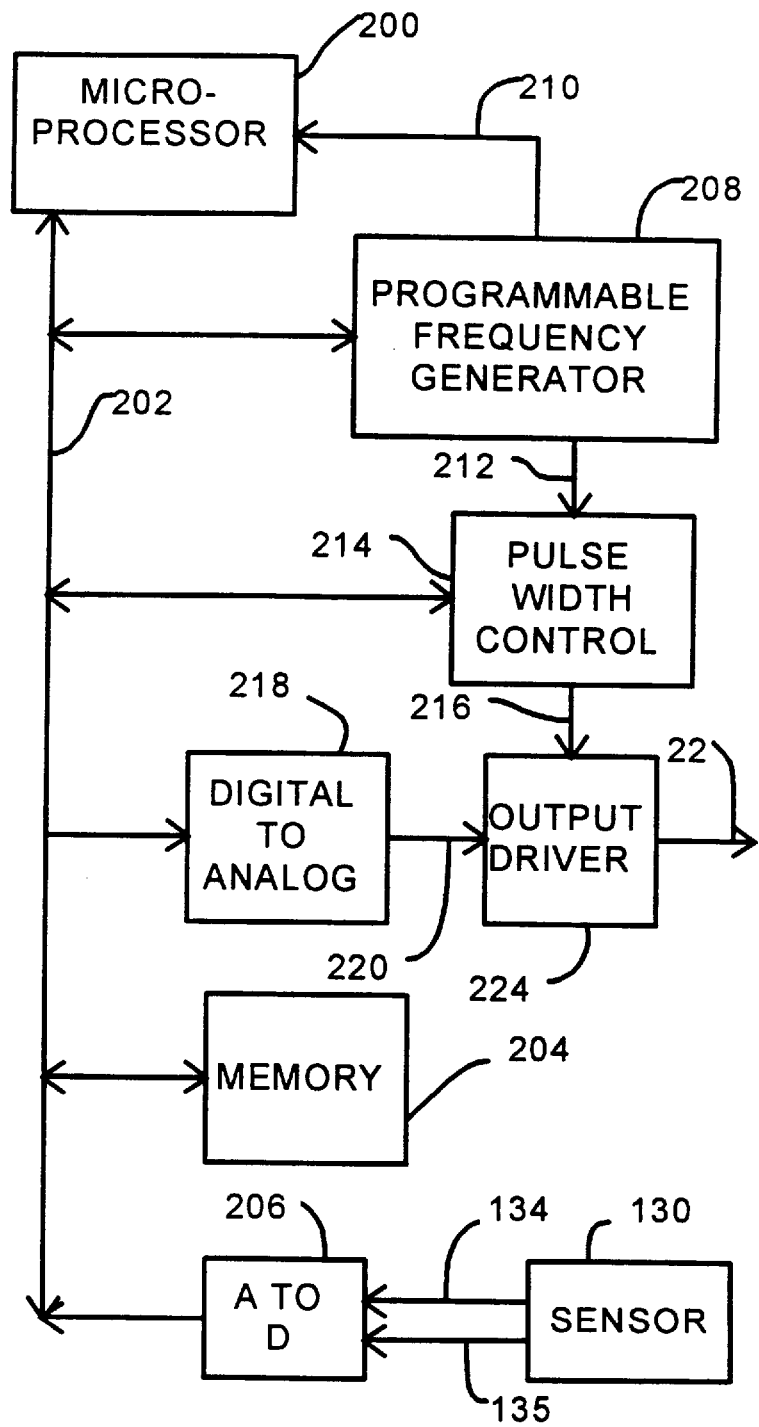
FIG. 3 is a schematic block diagram of a microprocessor and related circuitry used in the preferred embodiment of the invention.

For Dystonia, sensor 130 may take the form of a device for detecting relative motion of a joint or limb or muscle EMG. Referring to FIGS. 2 and 3, the output of sensor 130 is coupled by cable 132, comprising conductors 134 and 135, to the input of an analog to digital converter 206 within device 10.

Alternatively, the output of an external sensor would communicate with the implanted pulse generator through a telemetry downlink.

The remainder of the components shown in FIG. 3 are included in device 10. The output of the analog to digital converter 206 is connected to a microprocessor 200 through a peripheral bus 202 including address, data and control lines. Microprocessor 200 processes the sensor data in different ways depending on the type of transducer in use. When the signal on sensor 130 exceeds a level programmed by the clinician and stored in a memory 204, increasing amounts of stimulation will be applied through an output driver 224.

The stimulus pulse frequency is controlled by programming a value to a programmable frequency generator 208 using bus 202. The programmable frequency generator provides an interrupt signal to microprocessor 200 through an interrupt line 210 when each stimulus pulse is to be generated. The frequency generator may be implemented by model CDP1878 sold by Harris Corporation.

The amplitude for each stimulus pulse is programmed to a digital to analog converter 218 using bus 202. The analog output is conveyed through a conductor 220 to an output driver circuit 224 to control stimulus amplitude.

Microprocessor 200 also programs a pulse width control module 214 using bus 202. The pulse width control provides an enabling pulse of duration equal to the pulse width via a conductor 216. Pulses with the selected characteristics are then delivered from device 10 through cable 22 and lead 22A to the basal ganglia, thalamus or other region of the brain.

Microprocessor 200 executes an algorithm shown in FIGS. 4–8 in order to provide stimulation with closed loop feedback control. At the time the stimulation device 10 is implanted, the clinician programs certain key parameters into the memory of the implanted device via telemetry. These parameters may be updated subsequently as needed. Step 400 in FIG. 4 indicates the process of first choosing whether the neural activity at the stimulation site is to be blocked or facilitated (step 400(1)) and whether the sensor location is one for which an increase in the neural activity at that location is equivalent to an increase in neural activity at the stimulation target or vice versa (step 400(2)). Next the clinician must program the range of values for pulse width (step 400(3)), amplitude (step 400(4)) and frequency (step 400(5)) which device 10 may use to optimize the therapy. The clinician may also choose the order in which the parameter changes are made (step 400(6)). Alternatively, the clinician may elect to use default values.

Figure 4:
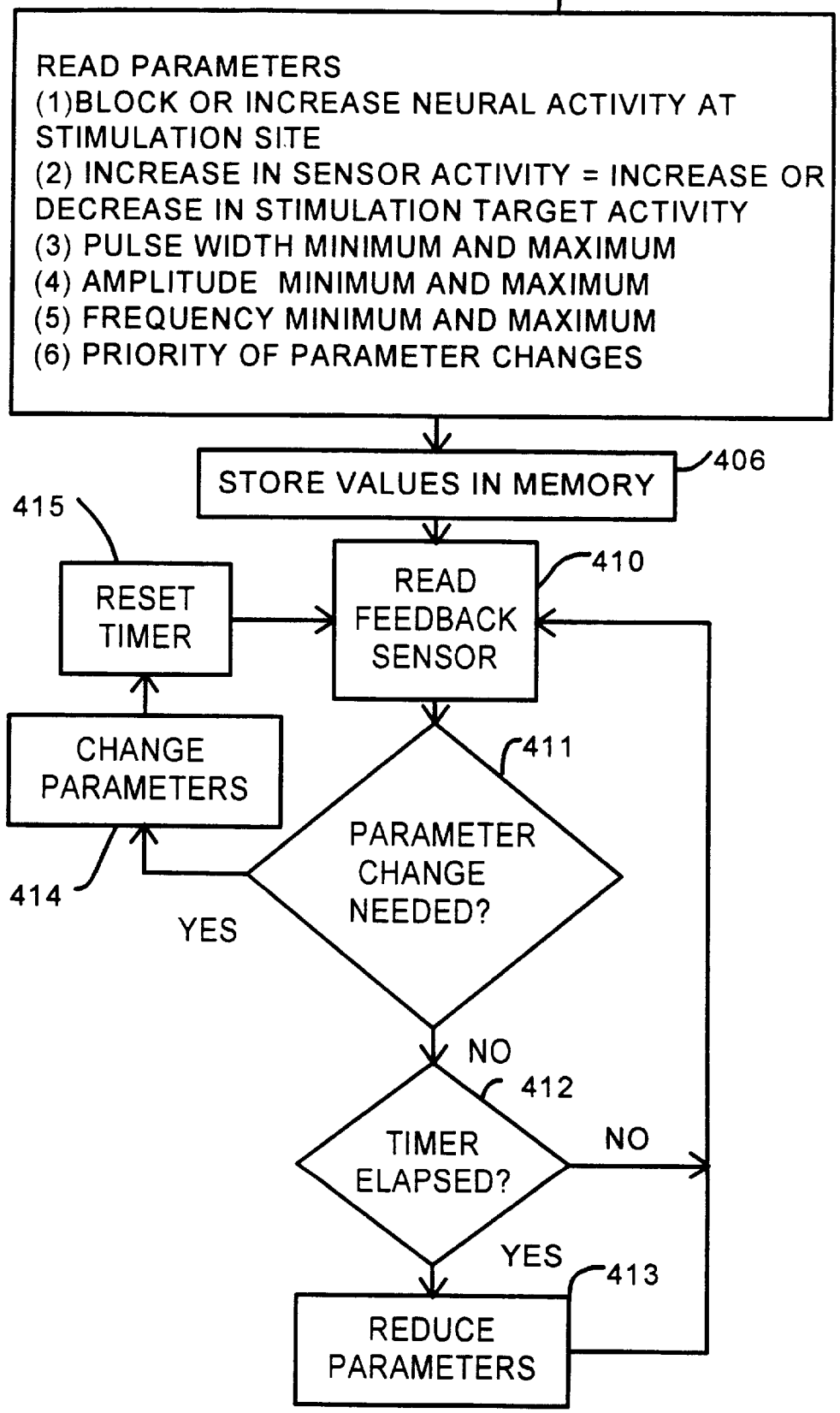
FIGS. 4–8 are flow charts illustrating a preferred form of a microprocessor program for generating stimulation pulses to be administered to the brain.

The algorithm for selecting parameters is different depending on whether the clinician has chosen to block the neural activity at the stimulation target or facilitate the neural activity. FIG. 4 details steps of the algorithm to make parameter changes.

Figure 5:
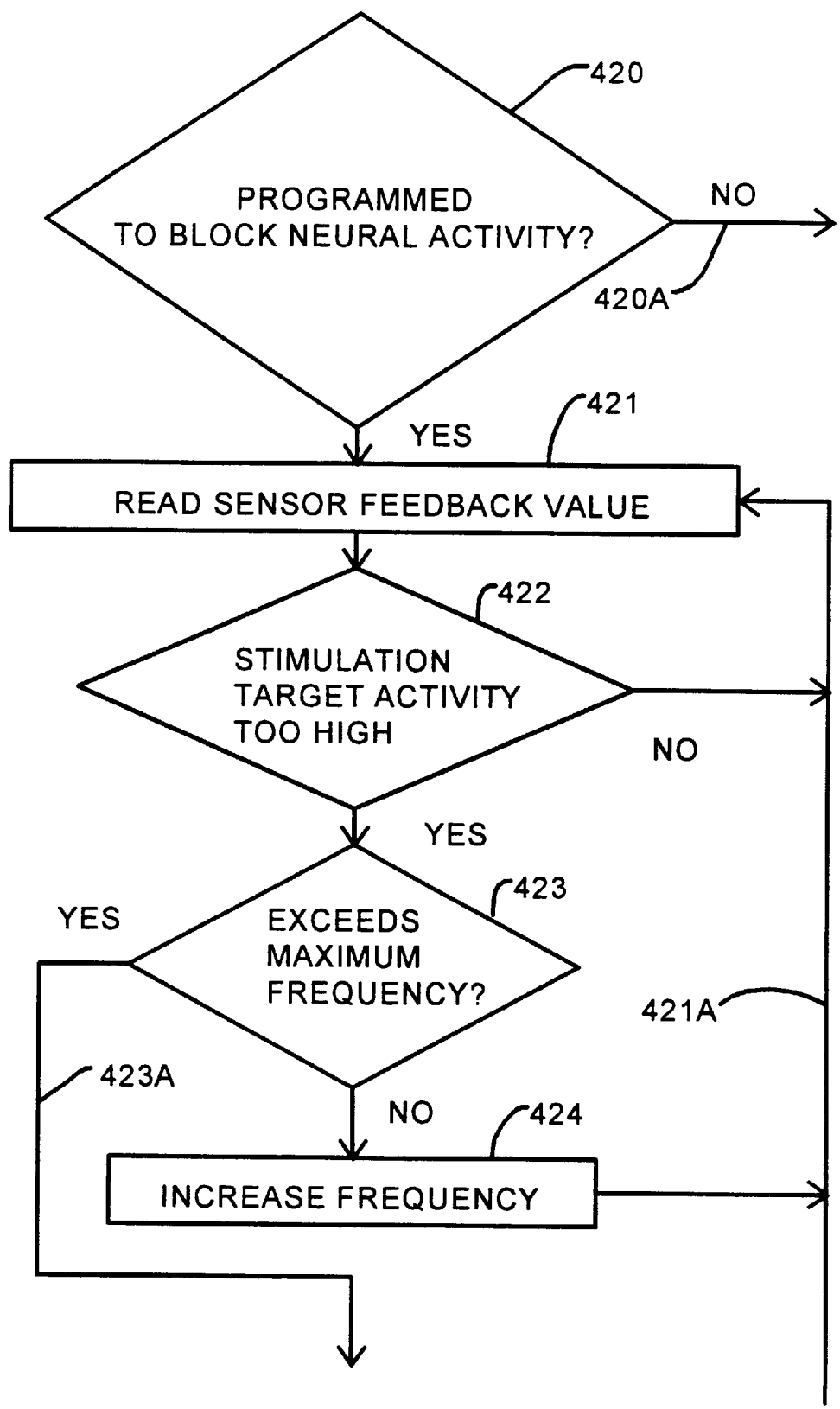
Figure 6:
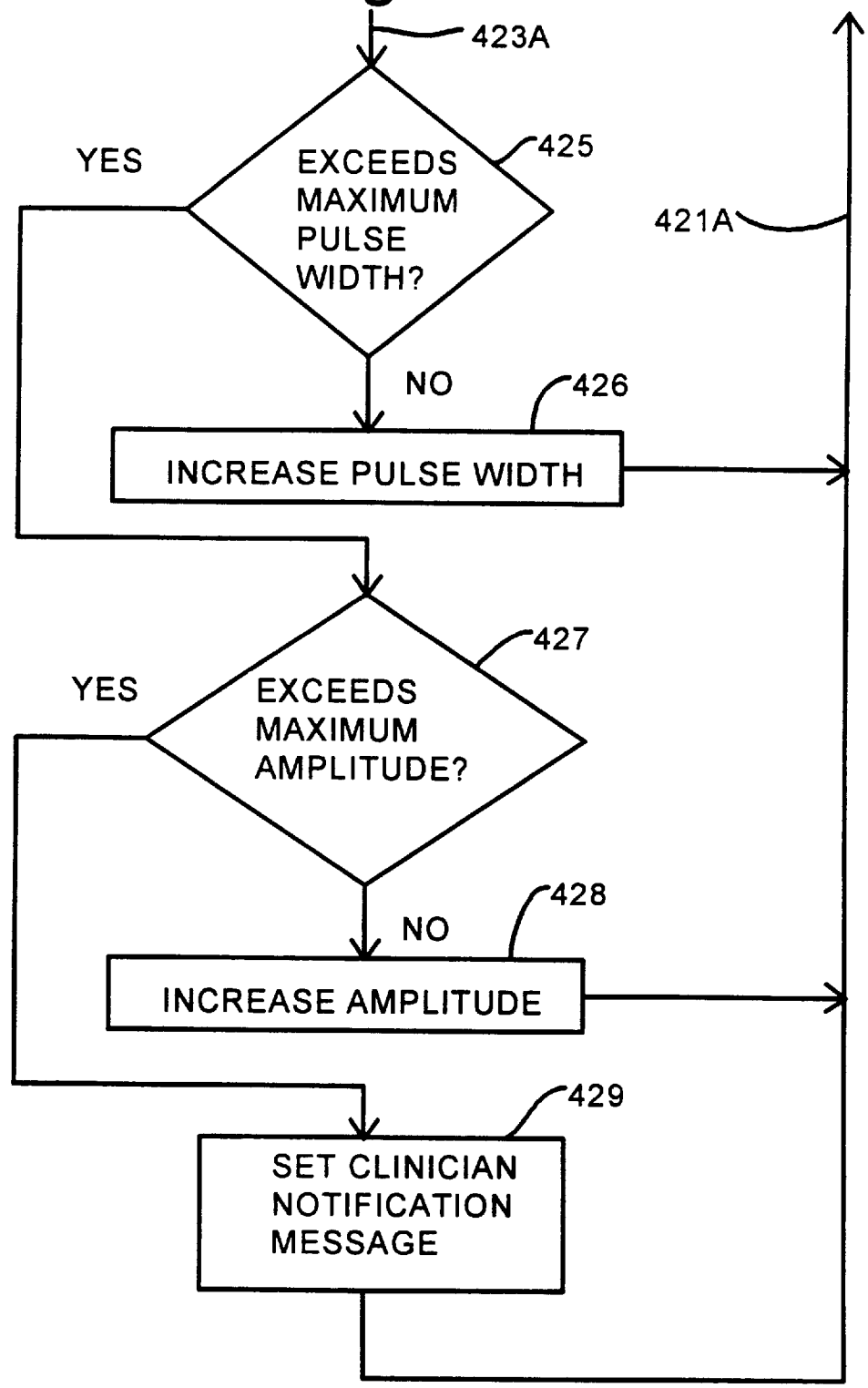
Figure 7:
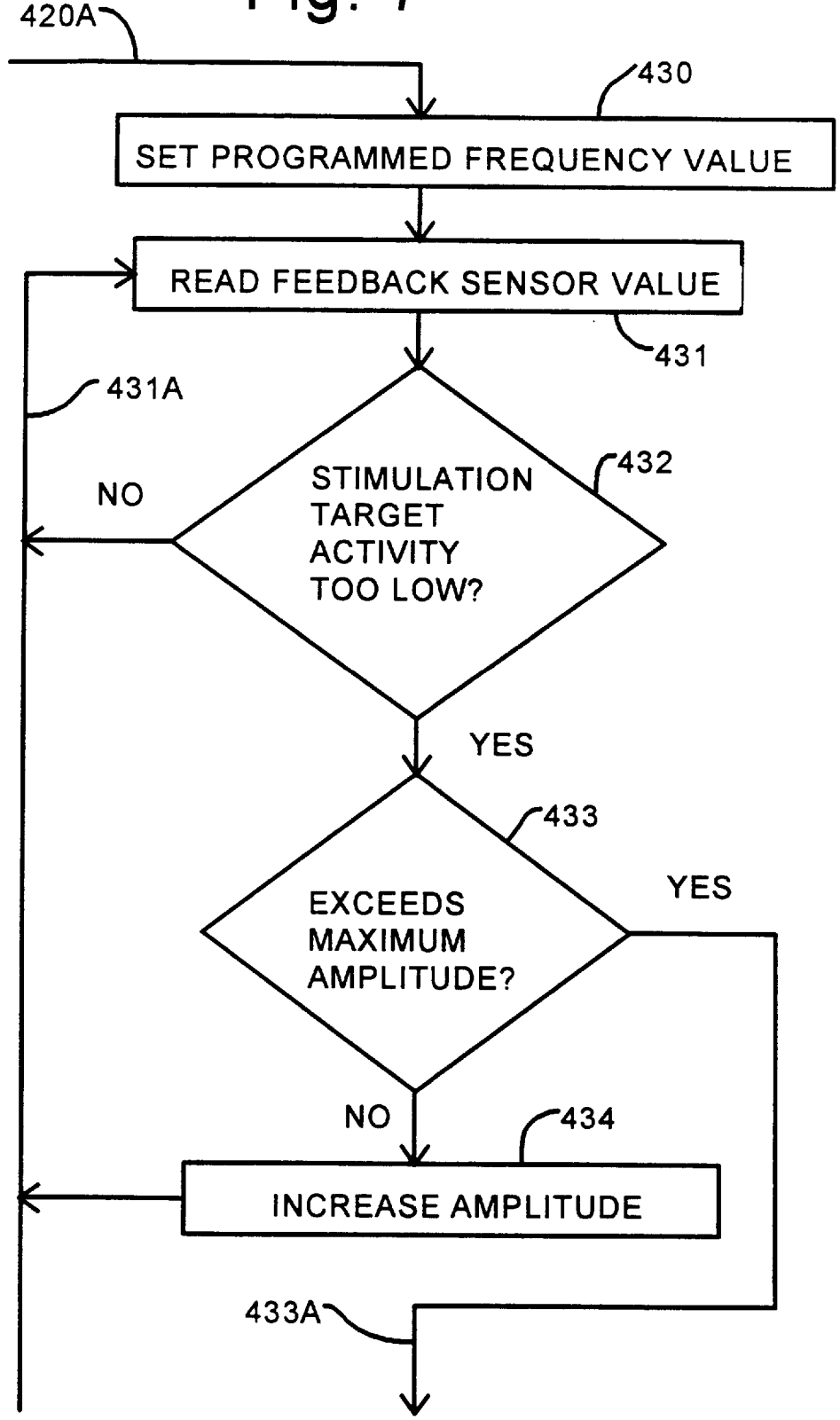

The algorithm uses the clinician programmed indication of whether the neurons at the particular location of the stimulating electrode are to be facilitated or blocked in order to reduce the neural activity in the subthalarnic nucleus to decide which path of the parameter selection algorithm to follow (step 420, FIG. 5). If the neuronal activity is to be blocked, device 10 first reads the feedback sensor 130 in step 421. If the sensor values indicate the activity in the glutamatergic neurons is too high (step 422), the algorithm in this embodiment first increases the frequency of stimulation in step 424 provided this increase does not exceed the preset maximum value set by the physician. Step 423 checks for this condition. If the frequency parameter is not at the maximum, the algorithm returns to step 421 through path 421A to monitor the feed back signal from sensor 130 If the frequency parameter is at the maximum, the algorithm next increases the pulse width in step 426 (FIG. 6), again with the restriction that this parameter has not exceeded the maximum value as checked for in step 425 through path 423A. Not having reached maximum pulse width, the algorithm returns to step 421 to monitor the feedback signal from sensor 130. Should the maximum pulse width have been reached, the algorithm next increases amplitude in a like manner as shown in steps 427 and 428. In the event that all parameters reach the maximum, a notification message is set in step 429 to be sent by telemetry to the clinician indicating that device 10 is unable to reduce neural activity to the desired level.

Figure 8:
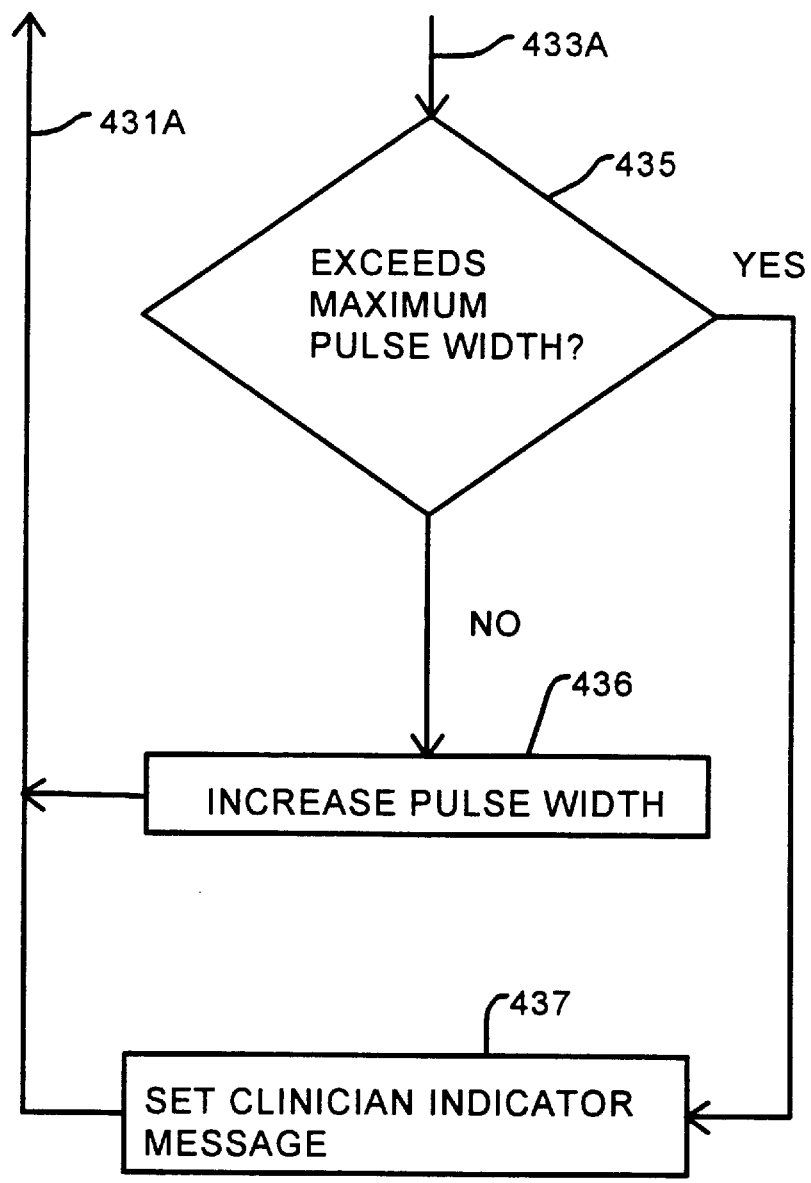

If, on the other hand, the stimulation electrode is placed in a location which the clinician would like to activate in order to increase an inhibition of the subthalamic nucleus, the algorithm would follow a different sequence of events. In the preferred embodiment, the frequency parameter would be fixed at a value chosen by the clinician to facilitate neuronal activity in step 430 (FIG. 7) through path 420A. In steps 431 and 432 the algorithm uses the values of the feedback sensor to determine if neuronal activity is being adequately controlled. In this case, inadequate control indicates that the neuronal activity of the stimulation target is too low. Neuronal activity is increased by first increasing stimulation amplitude (step 434) provided it doesn't exceed the programmed maximum value checked for in step 433. When maximum amplitude is reached, the algorithm increases pulse width to its maximum value in steps 435 and 436 (FIG. 8). A lack of adequate reduction ot neuronal activity in the subthalamic nucleus, even though maximum parameters are used, is indicated to the clinician in step 437. After steps 434, 436 and 437, the algorithm returns to step 431 through path 431 A, and the feedback sensor again is read.

It is desirable to reduce parameter values to the minimum level needed to establish the appropriate level of neuronal activity in the subthalarnic nucleus. Superimposed on the algorithm just described is an additional algorithm to readjust all the parameter levels downward as far as possible. In FIG. 4, steps 410 through 415 constitute the method to do this. When paramieters are changed, a timer is reset in step 415. If there is no need to change any stimulus parameters before the timer has counted out, then it may be possible due to changes in neuronal activity to reduce the parameter values and still maintain appropriate levels of neuronal activity in the target neurons. At the end of the programmed time interval, device 10 tries reducing a parameter in step 413 to determine if control is maintained. If it is, the various parameter values will be ratcheted down until such time as the sensor values again indicate a need to increase them. While the algorithms in FIG. 4 follow the order of parameter selection indicated, other sequences may be programmed by the clinician.

The present invention may be implemented by providing pulses to lead 22A having amplitudes of 0.1 to 20 volts, pulse widths varying from 0.02 to 1.5 milliseconds, and repetition rates varying from 2 to 2500 Hz. The appropriate stimulation pulses are generated by device 10 based on the computer algorithm shown in FIGS. 4–8 that read the output of converter 140 and makes the appropriate analysis.

For some types of motion disorders, a microprocessor and analog to digital converter will not be necessary. The output from sensor 130 can be filtered by an appropriate electronic filter in order to provide a control signal for device 10.

The type of stimulation administered by device 10 to the brain depends on the specific location at which the electrodes 115 of lead 22A are surgically implanted. The appropriate stimulation for the portion of the basal ganglia or thalamus in which lead 22A terminates, together with the effect of the stimulation on that portion of the brain for hyperkinetic motion disorders is provided in the following Table I:

TABLE I

| EFFECT | STIMULUS TYPE | LOCATION |
|---|---|---|
| DECREASE EXCITATION OF VL THALAMUS | HIGH FREQ. BLOCKING STIMULATION | VL THALAMUS |
| INCREASE INHIBITION OF VL THALAMUS | LOW FREQ. ACTIVATING STIMULATION | Pallido-thalamic axons (AL and LT) |
| INCREASE EXCITATION OF GPi/SNr | LOW FREQ. ACTIVATING STIMULATION | GPi/SNr |
| INCREASE EXCITATION OF GPi/SNr | LOW FREQ. ACTIVATING STIMULATION | Subthalamic to pallidal fiber tracts |
| DECREASE INHIBITION OF GPi/SNr | HIGH FREQ. BLOCKING STIMULATION | Neostriatum |
| INCREASE EXCITATION OF STN | LOW FREQ. STIMULATION | STN Nucleus |
| DECREASE INHIBITION OF STN | HIGH FREQ. BLOCKING STIMULATION | GPe |
| DECREASE EXCITATION OF GPe | HIGH FREQ. BLOCKING STIMULATION | GPe |
| INCREASE INHIBITION OF GPe | LOW FREQ. STIMULATION | Neostriatum |
| INCREASE INHIBITION OF GPe | LOW FREQ. STIMULATION | Putamen to Gpe fibers (i.e., border of nucleus) |

The appropriate stimulation for use in connection with the portion of the basal ganglia or thalamus in which lead 22A terminates, together with the effect of the stimulation on that portion of the brain for hypokinetic motion disorders is provided in the following Table II:

TABLE II

| EFFECT | STIMULUS TYPE | LOCATION |
|---|---|---|
| INCREASE EXCITATION OF VL THALAMUS | LOW FREQ. STIMULATION | VL THALAMUS |
| DECREASE INHIBITION OF VL THALAMUS | HIGH FREQ. BLOCKING STIMULATION | GPi/SNr |
| INCREASE INHIBITION OF GPi/SNr | LOW FREQ. STIMULATION | Striatopallidal fiber pathway |
| INCREASE INHIBITION OF GPi/SNr | LOW FREQ. STIMULATION | Neostriatum |
| DECREASE EXCITATION OF GPi/SNr | HIGH FREQ. BLOCKING STIMULATION | GPi/SNr |
| INCREASE INHIBITION OF STN | LOW FREQ. STIMULATION | GPe TO STN fiber pathway |
| INCREASE INHIBITION OF STN | LOW FREQ. STIMULATION | GPE |
| DECREASE EXCITATION OF STN | HIGH FREQ. BLOCKING STIMULATION | STN |
| INCREASE EXCITATION OF GPe | LOW FREQ. ACTIVATING STIMULATION | GPe |
| DECREASE INHIBITION OF GPe | HIGH FREQ. BLOCKING STIMULATION | Neostriatum |
| INCREASE INHIBITION OF GPi/SNr | LOW FREQ. ACTIVATING STIMULATION | Striatopallidal fiber pathways |

In the foregoing tables I and II, VL Thalamus means ventrolateral thalamus; GPi means internal segment of globus pallidus; SNr means substantia nigra pars reticulata, STN means subthalarnic nucleus; and GPe means external segment of globus pallidus; LT means lenticulo-thalamic fiber pathway and AL means ansa lenticularis.

Typical stereotaxic coordinates for the portions of a normal brain described in Tables I and II are identified in the following Table III:

TABLE III

| BRAIN REGION | MEDIAL-LATERAL DIMENSION | DORSAL-VENTRAL DIMENSION | ANTERIOR-POSTERIOR DIMENSION |
|---|---|---|---|
| VL Thalamus | 0.7 to 1.8 | 1.5 to −0.2 | 0.0 to −1.0 |
| Gpi | 0.5 to 2.0 | 0.5 to −0.7 | 0.7 to 2.0 |
| SNr | 0.5 to 1.5 | −0.6 to −1.5 | 0.7 to −0.7 |
| STN | 0.5 to 2.0 | 0.0 to −1.0 | 0.6 to −1.0 |
| GPe | 1.6 to 2.7 | 1.0 to −1.0 | 2.0 to −1.0 |
| Striatum: | | | |
| Caudate | 0.5 to 2.0 | 1.5 to 3.0 | 1.5 to 3.0 |
| Putamen | 1.2 to 3.3 | 1.5 to −1.0 | 2.5 to −1.2 |

In the foregoing table: the medial-lateral dimensions are relative to midline of the brain; the anterior-posterior dimensions are relative to the midpoint between the anterior commissure and posterior commissure with negative indicating the posterior direction; the dorsal-ventral dimensions are relative to a line connecting the midpoints of the anterior and posterior commissures with negative being ventral to the line; all dimension are in centimeters.

Microprocessor 200 within device 10 can be programmed so that the desired stimulation can be delivered to the specific brain sites described in Tables I and II. Alternatively, sensor 130 can be used with a closed loop feedback system in order to automatically determine the type of stimulation necessary to alleviate motor disorder symptoms as described in connection with FIG. 4 and 5.

By using the foregoing techniques, motor disorders can be controlled with a degree of accuracy previously unattainable.

Those skilled in that art will recognize that the preferred embodiments may be altered or amended without departing from the true spirit and scope of the invention, as defined in the accompanying claims.

We claim:

1. A system for treating a movement disorder resulting in abnormal motor behavior comprising in combination:

an implantable signal generator;

at least one implantable electrode coupled to said signal generator and adapted to be located in a brain and to stimulate at least one predetermined site in the brain;

a sensor for generating a signal related to the extent of said abnormal motor behavior; and control means responsive to said sensor signal for regulating said stimulation, whereby the stimulation is increased in response to an increase in said abnormal motor behavior and is decreased in response to a decrease in said abnormal motor behavior.

2. A system, as claimed in claim 1, wherein said sensor comprises a motion detector.

3. A system, as claimed in claim 1, wherein said sensor comprises means for detecting changes in potentials of or electromagnetic waves generated by muscle or nerve tissue.

4. A system, as claimed in claim 1, wherein said control means comprises a microprocessor.

5. A system, as claimed in claim 4, wherein said microprocessor includes means for executing an algorithm to provide stimulation with closed-loop feedback control.

6. A system, as claimed in claim 1, wherein said control means comprises an electrical filter.

7. A system, as claimed in claim 1, wherein said movement disorder is a hyperkinetic disorder or a hypokinetic disorder and wherein said sensor is capable of sensing the extent of said hyperkinetic disorder or hypokinetic disorder.

8. A system, as claimed in claim 1, wherein said sensor communicates with said control means by a telemetry downlink.

9. A system, as claimed in claim 1, wherein said sensor is an accelerometer.

10. A system, as claimed in claim 1, wherein said sensor includes a device for detecting gravity direction.

11. A system, as claimed in claim 1, wherein said sensor includes a device for detecting force in muscles or joints.

12. A system, as claimed in claim 1, wherein said sensor includes a device for detecting posture of a patient.

13. A system, as claimed in claim 1, wherein said sensor includes at least one electrode.

14. A system, as claimed in claim 1, wherein said sensor includes a transducer consisting of at least one electrode with an ion selective coating.

15. A system, as claimed in claim 1, wherein said sensor includes a device for detecting relative motion of a joint or a limb or a muscle EMG.

16. A system, as claimed in claim 1, wherein said control means includes a programmable frequency generator.

17. A system, as claimed in claim 1, wherein said control means includes a pulse width control module.

18. A system, as claimed in claim 1, further comprising means to adjust at least one parameter of said control means.

19. A system for treating a movement disorder resulting in abnormal motor behavior comprising in combination:

an implantable signal generator;

at least one implantable electrode coupled to said signal generator and adapted to be located in a brain and to stimulate at least one predetermined site in the brain;

a sensor for generating a sensor signal related to the extent of said abnormal motor behavior; and a microprocessor responsive to said sensor signal for regulating said stimulation.

\* \* \* \* \*